US006286463B1

United States Patent
Sykes

(10) Patent No.: US 6,286,463 B1
(45) Date of Patent: Sep. 11, 2001

(54) THERAPEUTIC DEVICES

(75) Inventor: Ilene Sykes, Albany, NY (US)

(73) Assignee: Peppypet LLC, Albany, NY (US)

( * ) Notice: Subject to any disclaimer, the term of this patent is extended or adjusted under 35 U.S.C. 154(b) by 0 days.

(21) Appl. No.: 09/452,227

(22) Filed: Dec. 1, 1999

(51) Int. Cl.[7] .................................................. A01K 29/00
(52) U.S. Cl. ............................................................. 119/858
(58) Field of Search ................................... 119/850, 856, 119/858; 600/9, 15; 54/66, 79.1, 79.4, 82

(56) References Cited

U.S. PATENT DOCUMENTS

| 125,006 | 3/1872 | Bazault . |
|---|---|---|
| 3,943,912 | * 3/1976 | Nakayama ............................. 600/15 |
| 4,022,189 | 5/1977 | Boxer . |
| 4,162,672 | 7/1979 | Yazaki . |
| 4,216,743 | 8/1980 | Cohen . |
| 4,330,892 | 5/1982 | Fukushima . |
| 4,587,956 | 5/1986 | Griffin et al. . |
| 5,304,111 | 4/1994 | Mitsuno et al. . |
| 5,389,061 | 2/1995 | Nor . |
| 5,426,925 | 6/1995 | Smargiassi . |
| 5,626,099 | 5/1997 | Staller et al. . |
| 5,642,739 | 7/1997 | Fareed . |
| 5,782,743 | * 7/1998 | Russell ................................... 600/15 |
| 5,817,000 | 10/1998 | Souder . |
| 5,832,879 | * 11/1998 | Pitzen ................................... 199/858 |
| 5,894,816 | 4/1999 | Coiro, Sr. et al. . |
| 6,050,931 | * 4/2000 | Russell ................................... 600/15 |
| 6,139,486 | * 10/2000 | Matuszewsii et al. ................. 600/15 |

FOREIGN PATENT DOCUMENTS

| WO 93/06887 | 4/1993 | (WO) . |
| WO 98/31422 | 7/1998 | (WO) . |
| WO 99/19023 | 4/1999 | (WO) . |

OTHER PUBLICATIONS

SharperImage.com, Magnetic Therapy (not dated).
Magnetic Pet Products, "Pet Pal Please Puppies!" Website printout, Nov. 10, 1999.
Nikken Wellness Technology for Living US Catalogue, Oct. 1999, first page and last page and pp. 28–33.

* cited by examiner

Primary Examiner—Thomas Price
(74) Attorney, Agent, or Firm—Hoffman, Warnick & D'Alessandro LLC; Spencer K. Warnick

(57) ABSTRACT

Therapeutic devices for animals that either include magnets or are made of magnetic material and are usable with an animal restraint. Also, a magnetic animal identification tag.

15 Claims, 6 Drawing Sheets

THERAPEUTIC DEVICES

BACKGROUND OF THE INVENTION

1. Technical Field

The present invention relates generally to therapeutic devices. More specifically, it relates to magnetic therapy devices for animals.

2. Related Art

It is recognized that selective placement of magnets on humans and animals has had some therapeutic effects on the treatment of various ailments such as arthritis and circulatory problems. Various biomagnet therapy devices now come in the form of wraps, bands or blankets. See, for example, U.S. Pat. No. 5,832,879 to Pitzen, U.S. Pat. No. 3,943,912 to Nakayama, and U.S. Pat. No. 5,426,925 to Smargiassi. A problem with these devices is that they are either unworkable for animals or not readily adjustable for different size animals. For instance, a small dog does not require the magnet strength applied to a cow or a horse.

Another shortcoming of the related art is the need to purchase an animal restraint made especially for magnet therapy apart from conventional animal restraints. Such a device is exemplified by "Magnetic Pet Products" in which magnets are built into a pet collar. As a result, when therapy is not desired, another collar must be purchased.

In view of the foregoing, there is a need for a therapeutic device providing adjustability of magnet strength and usage with conventional animal restraints.

SUMMARY OF THE INVENTION

The invention provides a therapeutic device usable with conventional animal restraints, such as harnesses or collars, and a magnetic animal identification tag. In one aspect of the invention a therapeutic device is provided including a contiguous hollow member; a pocket coupled to the contiguous hollow member, the pocket having a closure device attached thereto for closing the pocket; and at least one magnet positioned within the pocket.

Another aspect of the invention supplies a magnetic therapy device for directing a therapeutically effective magnetic flux into an animal including a contiguous hollow member; a pocket coupled to the hollow member, the pocket having a closure device attached thereto for closing the pocket; at least one magnet positioned within the pocket; and an animal restraint for attachment to an animal, the animal restraint having at least one part thereof extending through the hollow member to hold the hollow member adjacent the animal.

Another aspect of the invention provides an apparatus having: an elongate member having a first hollow area and at least one adjacent second hollow area, the first hollow area open at both ends of the elongate member; at least one magnet positioned within the at least one second hollow area; and an animal restraint having at least one portion thereof extending through the first area.

Yet another aspect of the invention includes a member made of a magnetic material and including an animal identifier thereon; and means for coupling the member to an animal restraint. In all of the above aspects, the strength of the magnet(s) may be adjusted according to desired effects, ailment, animal size, etc.

The above aspects provide therapeutic devices having adjustability of magnet strength and usage with conventional animal restraints.

Another aspect of the invention includes a therapeutic device including a hollow member made of a magnetic material; and an animal restraint having at least one portion thereof extending through the hollow member. This aspect provide a therapeutic device for use with conventional animal restraints. In one particular embodiment, the magnetic material is a magnetic fabric.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of the preferred embodiment.

Figure 1:
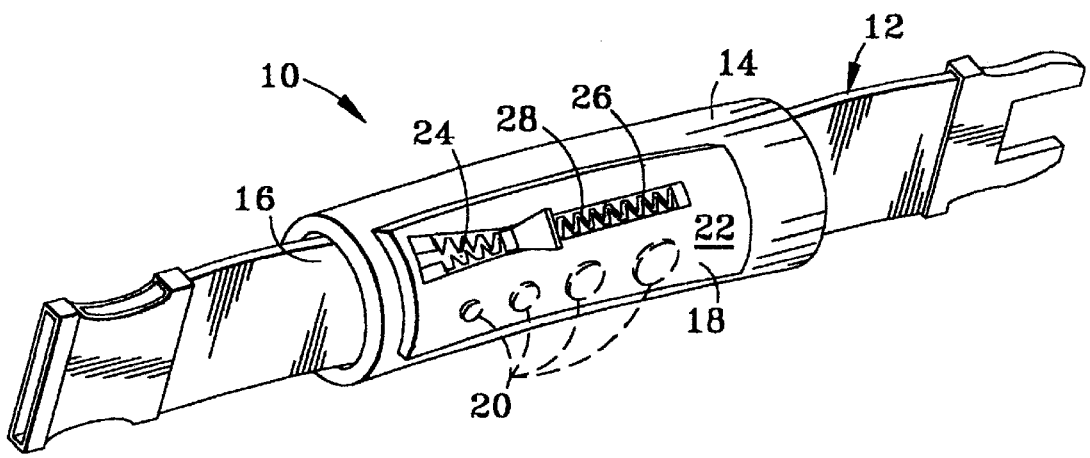
FIG. 1 shows a therapeutic device in accordance with the invention with an animal restraint.

FIG. 1 shows a therapeutic device 10 with an animal restraint 12. Device 10 includes a contiguous hollow member 14. Hollow member 14 may be made of a magnetic flux transparent material, and preferably a fabric such as natural or synthetic woven or non-woven material or blends thereof. One example that has been found advantageous is Lycra because its stretchability allows a variety of animal restraints 12 to be fed therethrough, as will be described below. Hollow member 14, however, may be made of any magnetic flux transparent material capable of receiving at least one portion 16 of animal restraint 12 therethrough.

A pocket 18 is coupled to hollow member 14 to hold at least one magnet 20 therein. Pocket 18 may be formed in a variety of ways. As shown in FIG. 1, pocket 18 may be formed by attaching a separate piece of fabric 22 to hollow member 14, e.g., by stitching. Pocket 18 preferably includes an opening 24 therein having a closure device 26 attached thereto for closing pocket 18. Pocket 18 may alternatively have an opening formed by an unstitched end thereof. Closure device 26 is preferably a zipper 28, but may also be any other well known closure device such as a hook and loop fastener.

Figure 2:
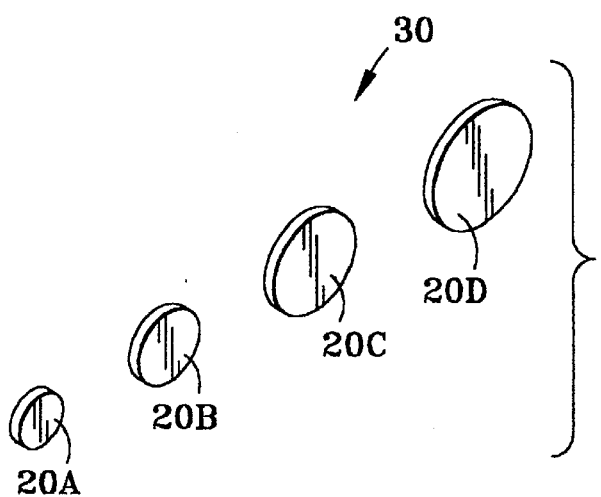
FIG. 2 shows a series of different strength magnets for use with the device of FIG. 1.

Referring to FIG. 2, a set of magnet(s) 30 may be provided for use with device 10. The magnets of set 30 may have different sized magnets 20A–20D and/or different gaussian strength magnets 20A–20D. Magnets 20A–20D may be shaped to fit within pocket 22. The shapes shown are for illustration purposes only. A user can choose a specific strength magnet 20 or group of magnets 20A–20D to attain a desired overall strength magnetic flux depending on, for example, the size of the animal to be treated. In most instances, however, magnet(s) 20 alone, or a combination thereof, provide a strength of at least 100 gauss and preferably about 400 gauss. Magnet(s) 20 may be made of any of a variety of magnetic material such as ferrite or ceramic-based magnetic material. While different polarity-type magnet(s) can be used, bi-polar magnets are preferred.

Figure 3:
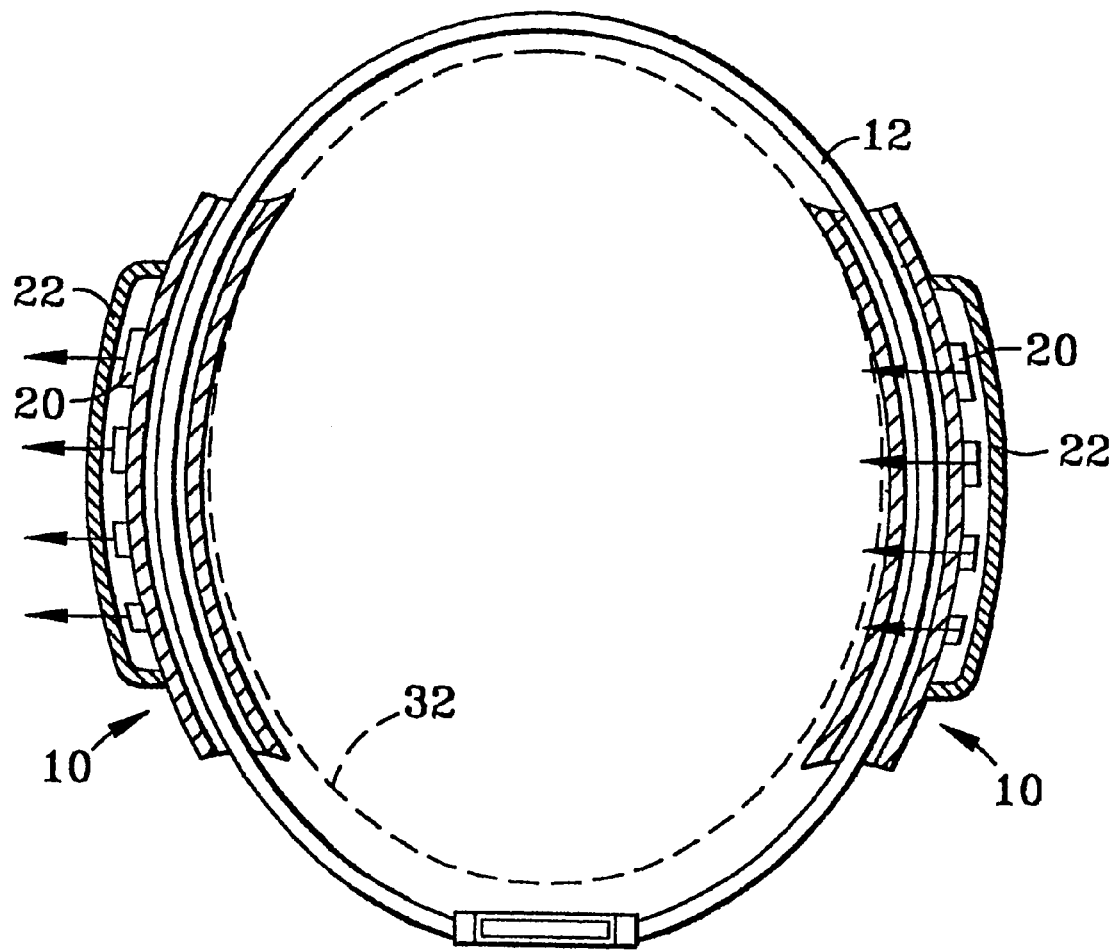
FIG. 3 shows a cross-sectional view of the invention in use with magnet(s) polarity facing in opposite directions.
Figure 4:
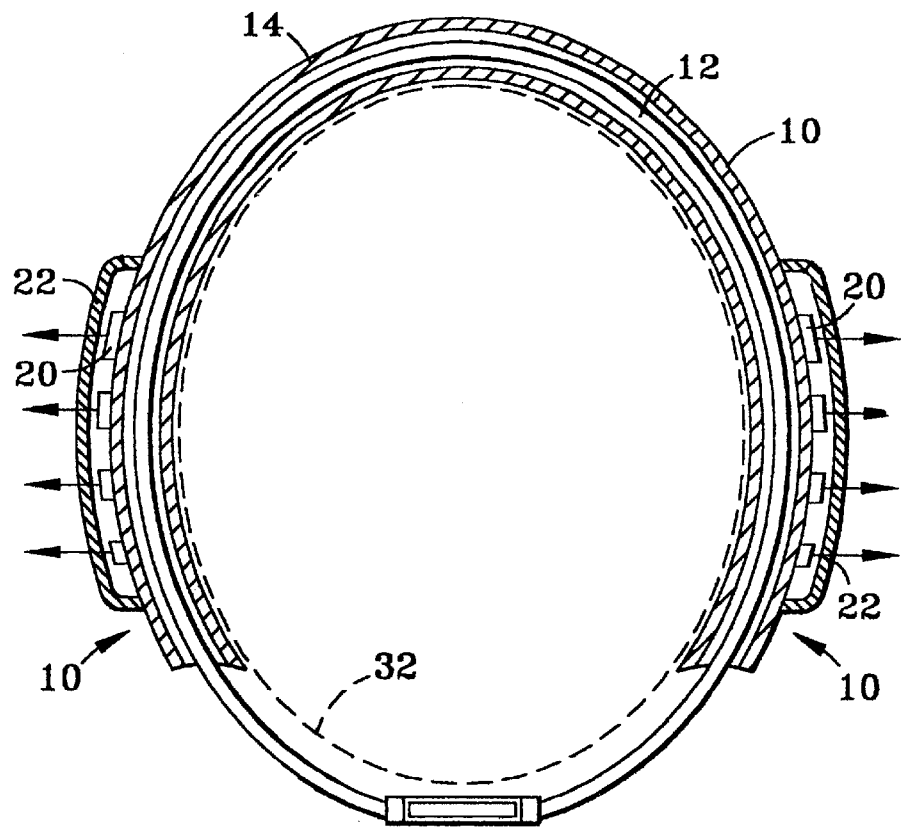
FIG. 4 shows a cross-sectional view of the invention in use with magnet(s) polarity facing in the same direction.

Referring to FIGS. 3 and 4, it should be recognized that one or more devices 10 may be provided on an animal restraint 12. Furthermore, a single device 10 may include one or more pockets 22. FIG. 3 illustrates how a plurality of devices 10 may be positioned about an animal restraint 12 coupled to an animal 32. FIG. 4 illustrates a single device 10 comprising two pockets 22, positioned about an animal restraint 12 coupled to an animal 32. It should be recognized that the position of pockets 22 may vary relative to animal restraint 12. For example, the positioning of device(s) 10 along the length, or on the inside/outside of animal restraint 12 may change. Also illustrated in FIGS. 3 and 4 is the polarity direction, indicated by arrows, of magnets 20. In FIG. 3, magnet(s) 20 are polarized in opposite directions perpendicular to hollow member 14, e.g., with an N pole of one set of magnet(s) 20 facing toward animal 32 and the N pole of another set of magnet(s) 20 facing away from animal 32. In FIG. 4, magnet(s) 20 are polarized in the same direction perpendicular to hollow member 14, e.g., with an N pole of all magnet(s) 20 facing away from (or toward) animal 32.

Figure 5:
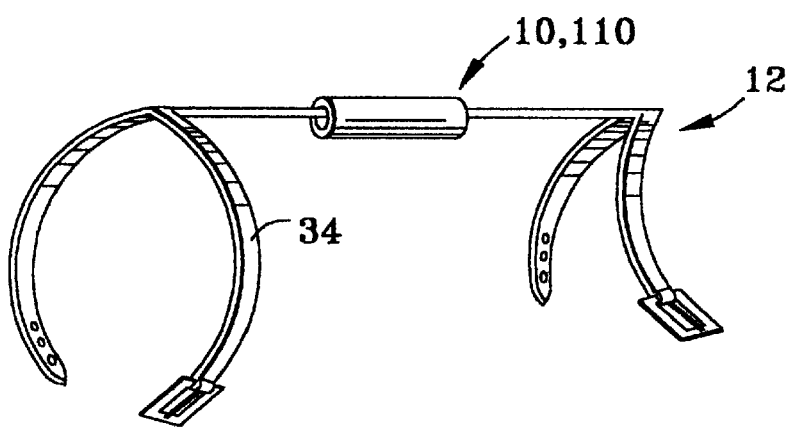
FIG. 5 shows an animal harness type animal restraint using the therapeutic device of FIG. 1.
Figure 6:
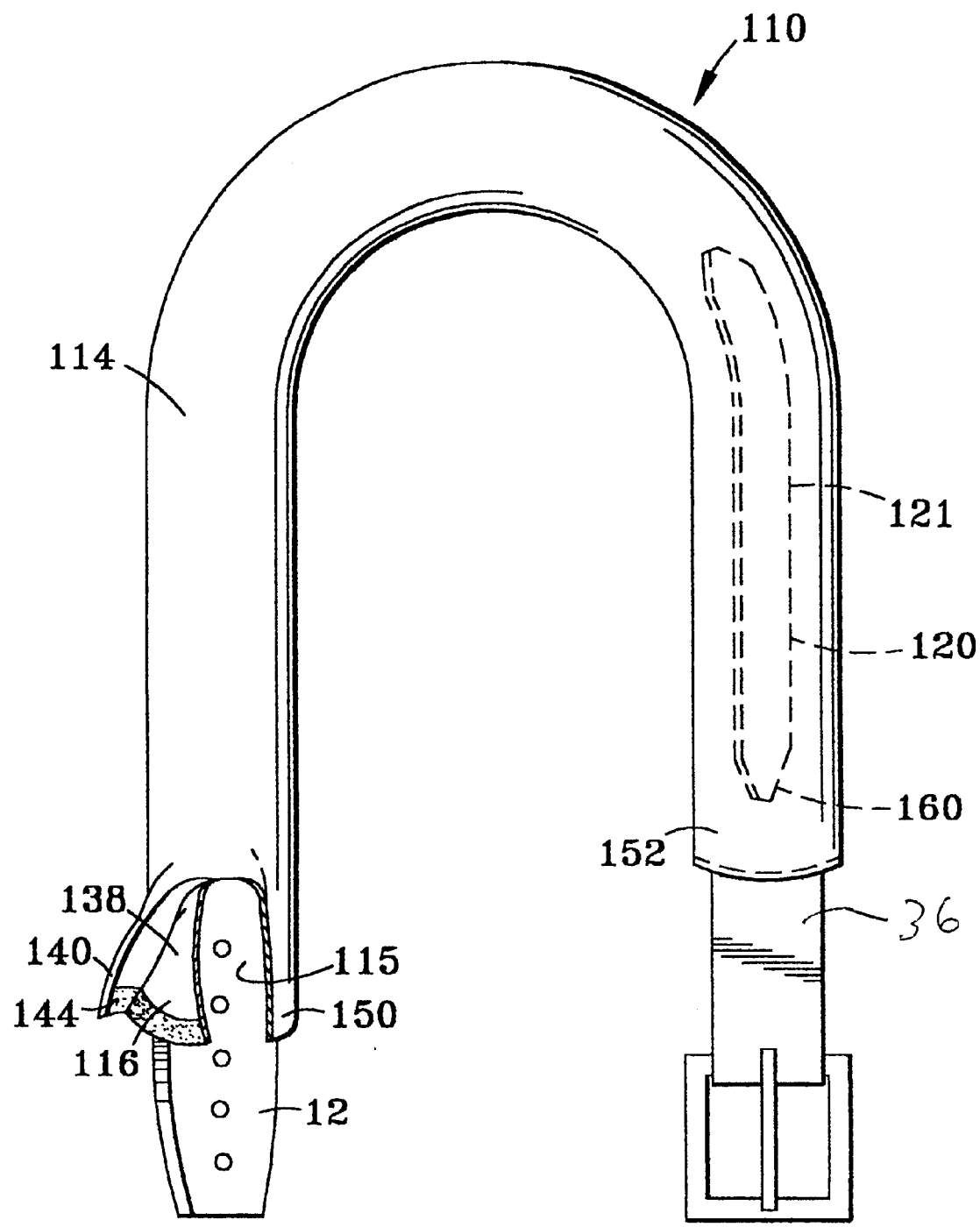
FIG. 6 shows a different type animal collar animal restraint using an alternative embodiment of the therapeutic device of FIG. 1.

Referring to FIGS. 5 and 6, various animal restraints 12 are illustrated. An animal restraint 12 is defined for purposes of this disclosure as any device capable of attachment to an animal. Such devices may be attached to the animal, for example, for restraining, clothing, decorating, applying therapy, etc. Accordingly, animal restraint 12 may take a variety of forms. Examples are a harness 34, shown in FIG. 5, capable of strapping around the neck and torso of an animal, and a collar 36, shown in FIG. 6. Animal restraint 12 can be made of a variety of materials. Common examples are woven synthetic material, leather, insect repellant material, etc.

Referring to FIGS. 6–10, alternative embodiments of the invention and, in particular, ways of forming a pocket to hold a magnet are illustrated. In the FIGS. 6 and 7 embodiments, therapeutic device 110 is provided as an elongate member 114 preferably formed by two substantially concentric fabric members 138, 140. Members 138, 140 are coupled to create a first hollow area 115 and at least one adjacent second hollow area or pocket 116.

Figure 7:
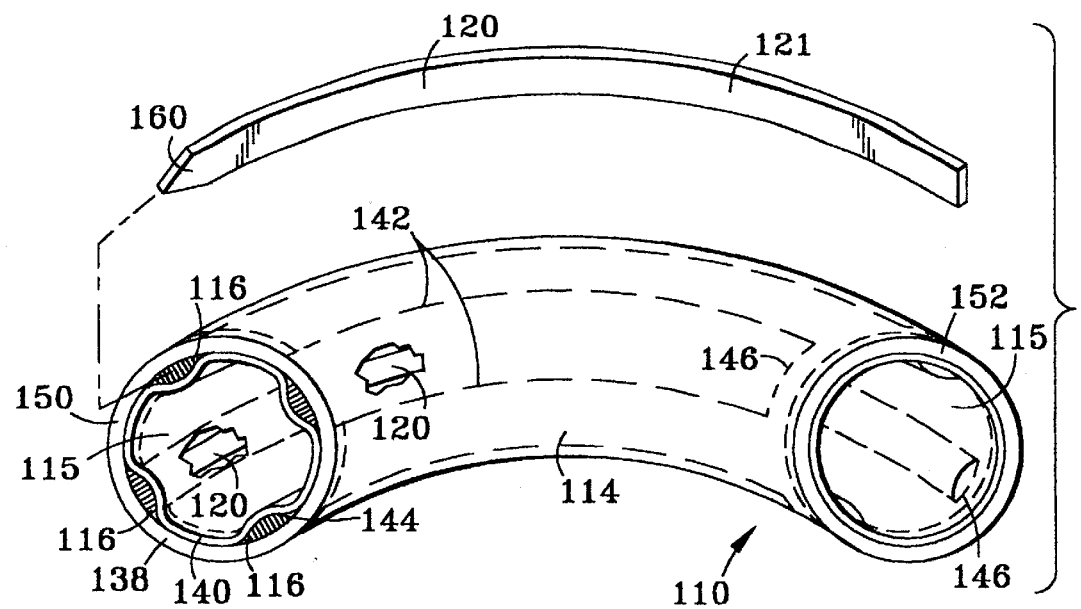
FIG. 7 shows an alternative embodiment of the therapeutic device of FIG. 1.

As shown in FIG. 7, if more than one second hollow area 116 is provided, they are preferably provided by stitching 142 extending along elongate member 114. Second hollow area(s) 116 includes a closure 144, preferably in the form of a hook and loop fastener, at a first end 150 of elongate member 114. At second end 152, each second hollow area(s) 116 is permanently closed prior to termination of first hollow area 115, for instance, by stitching 146 to form a pocket. If just one second hollow area 116 is provided, as shown in FIG. 6, then second end 152 may simply be stitched shut. First hollow area 115 is open at both ends 150, 152 of elongate member 114 and is capable of receiving an animal restraint 12 therethrough. For some embodiments, magnet(s) 120 are preferably provided in elongate strip form 121 such that they fit within second hollow area(s) 116 and can be held in place therein by closure(s) 144. Magnet(s) 120 may include pointed end(s) 160 to ease their insertion into second hollow area(s) 116.

Figure 8:
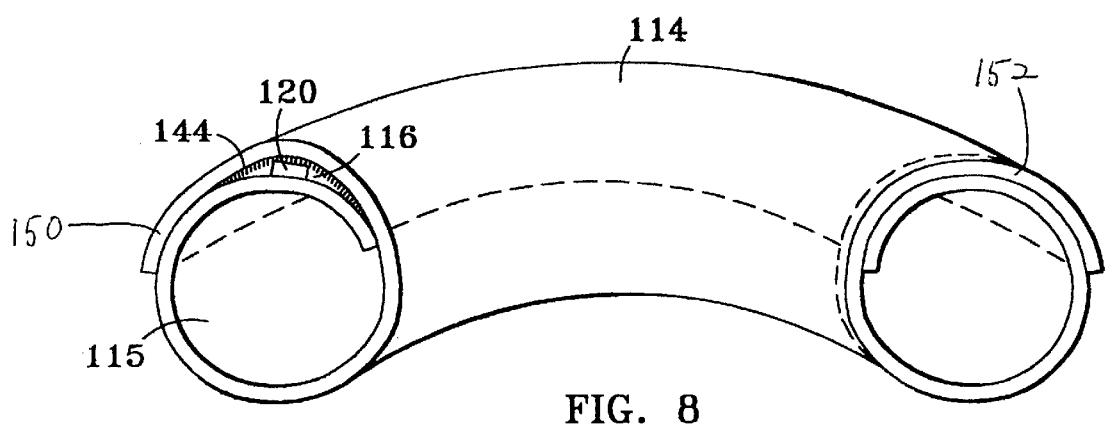
FIG. 8 shows an alternative embodiment of the therapeutic device of FIG. 1.

Referring to FIG. 8, elongate member 114 may be formed from a single piece of fabric that is stitched in an overlapped fashion to form first hollow area 115 and second hollow area 116. In this setting, first end 150 would include a closure 144 such as a hook and loop fastener, and second end 152 would be stitched shut permanently. Magnet(s) 120 would be inserted into second hollow area 116.

Figure 9:
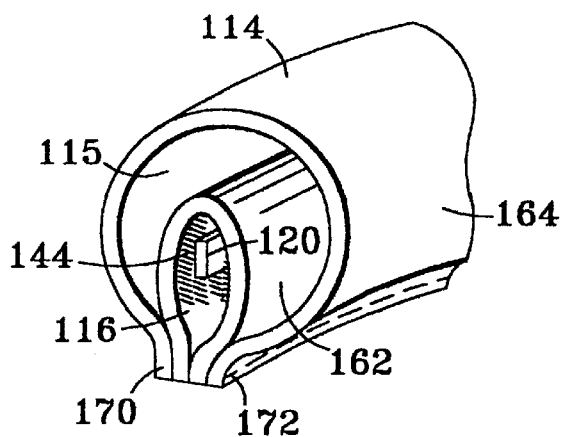
FIG. 9 shows an alternative embodiment of the therapeutic device of FIG. 1.
Figure 10:
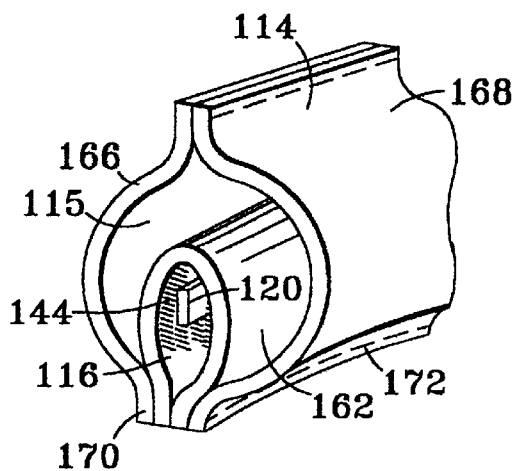
FIG. 10 shows an alternative embodiment of the therapeutic device of FIG. 1.

FIGS. 9 and 10 illustrate embodiments in which second hollow area 116 is formed by a piece of overlapped fabric 162. The rest of elongate member 114 and, in particular, first hollow area 115, may be formed either by a single piece of overlapped fabric 164 (FIG. 9), or two pieces of fabric 166, 168 (FIG. 10) stitched together along their lengths. In either setting it is preferred to stitch an overlap area 170 of the second hollow area fabric and elongate member fabric with a single stitch 172. Second hollow area 116 may include a closure 144 such as a hook and loop fastener and is preferably stitched shut at an opposite end (not shown).

Figure 11:
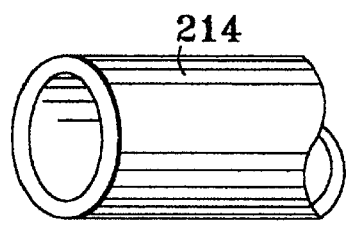
FIG. 11 shows an alternative embodiment of the therapeutic device of FIG. 1.

Referring to FIG. 11 an alternative embodiment of the invention is disclosed. In this embodiment, a hollow member 214 made of a magnetic material is provided. Preferably, the magnetic material is a magnetic fabric such as that used by Nikken Inc. to create their ELASTOMAG® line of products. Hollow member 214 receives at least one portion of an animal restraint therethrough, as described above. Hollow member 214 may be one integral piece, as shown in FIG. 11, one piece sewn to itself, similar to FIG. 9 but without the inner pocket, or numerous pieces of material, similar to FIG. 10 but without the inner pocket.

Figure 12:
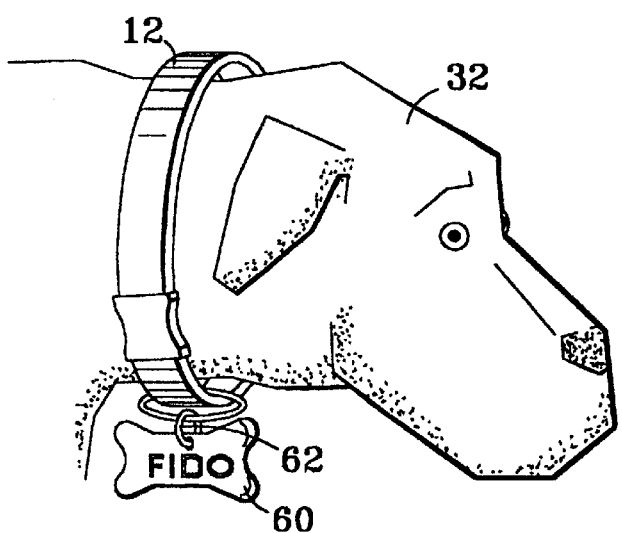
FIG. 12 shows a hanging magnetic animal identification tag.
Figure 13:
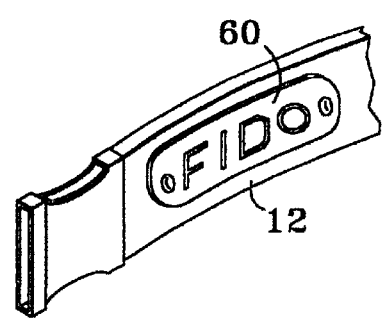
FIG. 13 shows a mounted magnetic animal identification tag.

Another mechanism for providing magnetic therapy to an animal includes an animal identification tag made of a magnetic material as shown in FIGS. 12 and 13. A member 60 is made of a magnetic material and includes an animal identifier thereon. Means for coupling member 60 to an animal restraint 12, as shown in FIGS. 12, may be provided, for example, by a hanging fastener 62 or by direct mounting, as shown in FIG. 13. Other means for coupling recognized in the art may also be used. Magnetic animal identification tag 60 may be used alone or in combination with therapeutic device 10, 110. As with magnet(s) 20, the strength of magnet 60 may be varied, for example, according to the size of animal 32 to which it is attached.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

I claim:

1. A magnetic therapy device for directing a therapeutically effective magnetic flux into an animal, the device comprising:
   a contiguous hollow member adapted to receive an animal restraint therethrough;
   a pocket coupled to the hollow member, the pocket having closure device attached thereto for closing the pocket, the pocket running substantially the entire length of the contiguous hollow member; and
   at least one magnet positioned within the pocket.

2. The device of claim 1, wherein the hollow member is made of a fabric.

3. The device of claim 1, further comprising an animal restraint for attachment to an animal, the animal restraint having at least one part thereof extending through the hollow member to hold the hollow member adjacent the animal.

4. The device of claim 3, wherein the animal restraint is a collar.

5. The device of claim 4, wherein the collar is made of an insect repellant material.

6. The device of claim 3, wherein the animal restraint is a harness.

7. The therapeutic device of claim 1, wherein the at least one magnet has a strength of at least 100 gauss.

8. The therapeutic device of claim 1, wherein the at least one magnet includes two magnets polarized in the same direction perpendicular to the hollow member.

9. The therapeutic device of claim 1, wherein the at least one magnet includes two magnets polarized in opposite directions perpendicular to the hollow member.

10. The therapeutic device of claim 1, wherein the hollow member is made of a magnetic flux transparent material.

11. The therapeutic device of claim 1, wherein the at least one magnet is a plurality of magnets.

12. The therapeutic device of claim 1, wherein the at least one magnet is a set of different strength magnets, whereby a user can choose a specific strength magnet or group of magnets to attain a desired overall strength magnetic flux.

13. An apparatus for directing a therapeutically effective magnetic flux into an animal, the apparatus comprising:
   an elongate member having a first hollow area and at least one adjacent second hollow area, wherein the first hollow area is open at both ends of the elongate member and the at least one second hollow area runs substantially the entire length of the elongate member; and
   at least one magnet positioned within the at least one second hollow area; wherein the apparatus is positionable adjacent an animal.

14. The apparatus of claim 13, wherein each second hollow area is permanently closed at one end and includes a closure device for closing the hollow area at the other end.

15. The apparatus of claim 13, wherein the at least one second hollow area is a plurality of hollow areas.

* * * * *